United States Patent
Rosenwasser

(10) Patent No.: US 6,337,052 B1
(45) Date of Patent: Jan. 8, 2002

(54) INSULATED SPECIMEN CONTAINER

(75) Inventor: George Rosenwasser, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/441,183

(22) Filed: Nov. 15, 1999

(51) Int. Cl.⁷ .............. B01L 3/00; B67D 5/06; B65D 37/00; B65D 6/12; A61B 17/06
(52) U.S. Cl. .......... 422/102; 422/99; 222/183; 222/188; 222/206; 206/438; 220/8
(58) Field of Search ............ 422/102; 222/183, 222/188, 206; 435/307.1; 206/438, 524.1, 524.6, 585; 220/8, 23.86, 23.87, 23.91

(56) References Cited

U.S. PATENT DOCUMENTS

| | | | |
|---|---|---|---|
| 2,940,641 A | * | 6/1960 | Norrish et al. ............ 222/183 |
| 2,991,923 A | * | 7/1961 | Wilson ..................... 229/51 |
| 2,998,165 A | * | 8/1961 | Elorza ..................... 222/182 |
| 3,369,121 A | * | 2/1968 | Bruno et al. ............... 250/106 |
| 3,819,040 A | * | 6/1974 | Coons ..................... 206/1 R |
| 3,844,407 A | * | 10/1974 | Buie ....................... 206/1.5 |
| 3,856,178 A | | 12/1974 | Nargaard |
| 4,411,575 A | * | 10/1983 | Miller ..................... 414/217 |
| 4,844,242 A | | 7/1989 | Chen et al. |
| 5,008,084 A | * | 4/1991 | Kelley ..................... 422/102 |
| 5,221,016 A | * | 6/1993 | Karpal ..................... 215/12.2 |
| 5,236,088 A | * | 8/1993 | Dhority et al. ............. 206/438 |
| 5,405,012 A | | 4/1995 | Shindler et al. |
| 5,427,741 A | * | 6/1995 | Bennett .................... 422/102 |
| 5,494,198 A | | 2/1996 | Heiberger et al. |
| 5,681,740 A | * | 10/1997 | Messier et al. ............. 435/284.1 |
| 5,823,342 A | * | 10/1998 | Caudilo et al. ............. 206/438 |
| 5,823,379 A | * | 10/1998 | Friendlander et al. ........ 220/408 |
| 5,827,385 A | * | 10/1998 | Meyer et al. ............... 156/87 |
| 5,941,583 A | * | 8/1999 | Raimondi .................. 294/1.2 |
| 5,972,292 A | * | 10/1999 | DeMeo ..................... 422/25 |
| 6,020,575 A | * | 2/2000 | Nagle et al. ............... 219/432 |
| 6,028,293 A | * | 2/2000 | Nagle et al. ............... 219/432 |
| 6,063,340 A | * | 5/2000 | Lewis et al. ............... 422/102 |
| 6,085,927 A | * | 7/2000 | Kusz ...................... 220/23.87 |
| 6,145,685 A | * | 11/2000 | Dick ...................... 220/23.88 |
| 6,199,699 B1 | * | 3/2001 | Eastman ................... 206/545 |
| 6,247,280 B1 | * | 6/2001 | Grinshpun et al. .......... 52/309.12 |

* cited by examiner

Primary Examiner—Jill Warden
Assistant Examiner—Brian R. Gordon
(74) Attorney, Agent, or Firm—Philip D. Freedman

(57) ABSTRACT

A container for storing and transporting a specimen under thermally stable conditions includes an outer insulating container body having a top and sidewall to form a receptacle shape and an inner insulating container body having a bottom and sidewall to form a receptacle shape to fit in interlocking nested engagement with the outer insulating container body to form a double walled hermetic chamber. A specimen receiving structure is supported within the hermetic chamber for receiving a biological specimen such as a corneal tissue. Another comprises an outer insulating container body and an inner insulating container body shaped to fit in interlocking nested engagement with the outer insulating container body to form a hermetic chamber. At least one of the insulating bodies comprises a hard shell filled with an insulating material.

22 Claims, 3 Drawing Sheets

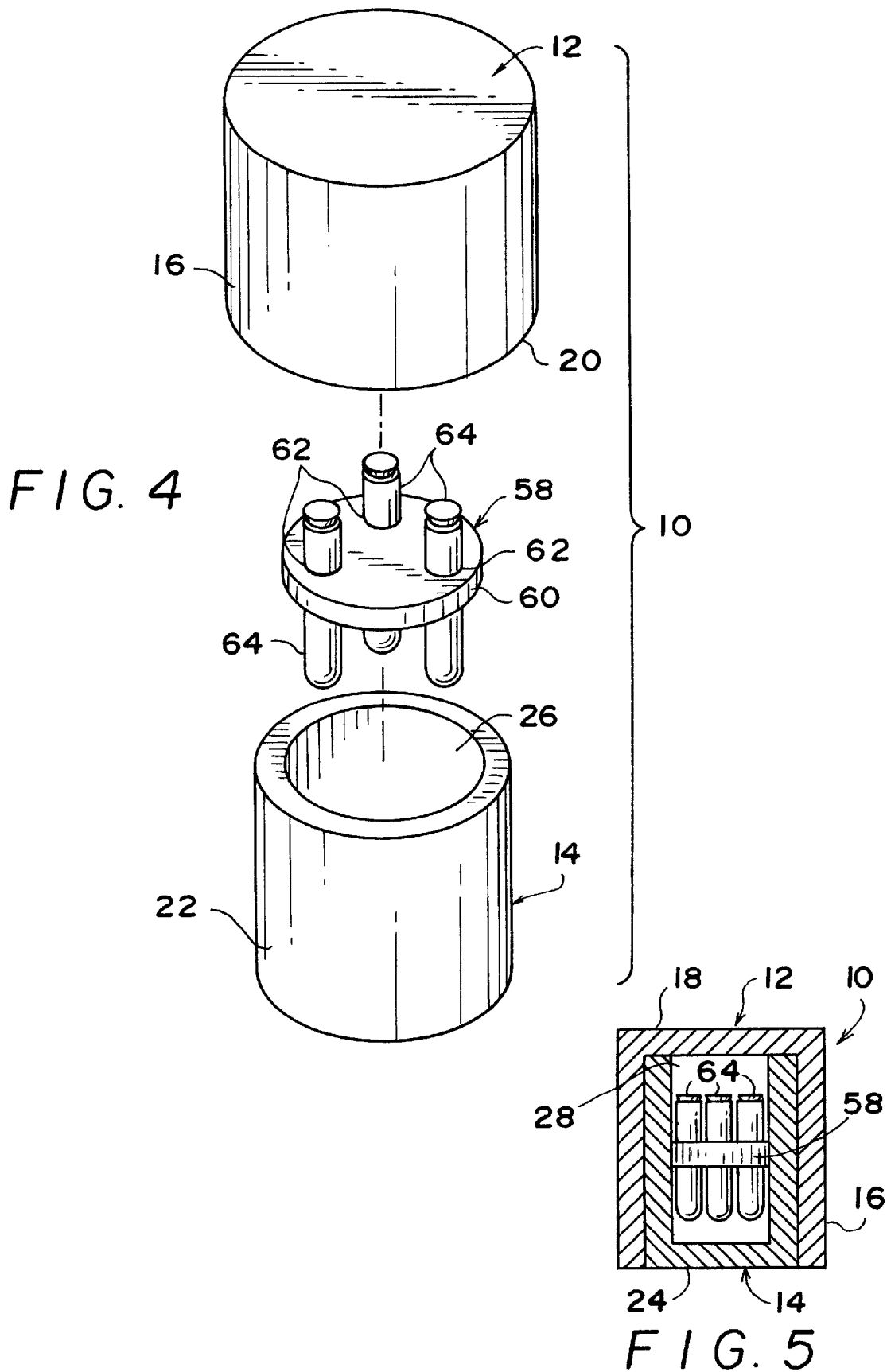

INSULATED SPECIMEN CONTAINER

BACKGROUND OF THE INVENTION

The present invention relates to an insulated container suitable for storing and transporting temperature sensitive specimens. In particular, the invention relates to a container for storing and transporting biological specimens such as corneal tissue.

A biological specimen for transplant comprises living cells or tissue that produce a biologically active molecule or impart a required biological function to an individual. Generally, the specimen is tissue that includes a semipermeable membrane that permits diffusion of nutrients to cells and allows secreted cellular products and waste materials to diffuse away from cells.

An eye cornea is a common type of transplantable biological specimen. For example, a donor cornea is utilized in keratoplasty, a procedure for restoring sight in patients with cornea opacity. The corneal tissue is typically shipped from location to location or stored for use in the operative procedure. The number of available corneas for this procedure is dependent to a large degree on proper storage and transport of the cornea between the time it becomes available from a donor and the time it is used in the operative procedure. Extending cornea preservation time and protecting the cornea increases the quantity and quality of tissues available for transplant.

Temperature is a significant problem in the storage and transport of corneal transplant tissue. Increased temperature increases the metabolic activity and decreases tissue viability of the cornea. Current data indicate that corneal tissue should be stored in a safe range of about 2° to about 6° C. Higher temperature can allow tissue necrosis to begin, while lower temperature may damage cells and cause decreased viability.

Additionally, improper positioning during transport or storage can damage the surface of corneal tissue. The cornea can rub against structural aspects of a carrier case to damage the cornea endothelial layer.

There is a need to provide an inexpensive and easy to construct storage and transport container that protectively positions a temperature sensitive specimen and that maintains temperature of the storage environment within a protective range.

SUMMARY OF THE INVENTION

The invention provides a container for storing and transporting a temperature sensitive specimen under thermally stable conditions to minimize damage during transportation and storage. The container comprises an outer insulating container body having a top and sidewall to form a receptacle shape and an inner insulating container body having a bottom and sidewall to form a receptacle shape to fit in interlocking nested engagement with the outer insulating container body to form a double walled hermetic chamber. A specimen receiving structure is supported within the hermetic chamber for receiving a biological specimen such as a corneal tissue.

In another embodiment, a container is provided for transporting temperature sensitive material, wherein the container comprises an outer insulating container body and an inner insulating container body shaped to fit in interlocking nested engagement with the outer insulating container body to form a hermetic chamber. At least one of the insulating bodies comprises a hard shell filled with an insulating material.

BRIEF DESCRIPTION OF THE DRAWINGS

FIG. 4 is an exploded schematic representation of another embodiment of the container; and FIG. 5 is a schematic cut-away representation of the embodiment.

DETAILED DESCRIPTION OF THE INVENTION

The container of the invention has particular use with a biological specimen, such as a corneal tissue that is transported and stored for implantation into a recipient. The container is inexpensive and easy to manufacture. The container can provide an airtight hermetic seal and protection for the retained specimen from temperature variation. When the outer insulating container body and the inner insulating container body are secured to one another, a retained specimen can be completely isolated from direct shock.

These and other features will become apparent from the following drawing and detailed discussion, which by way of example without limitation describe embodiments of the present invention.

Figure 1:
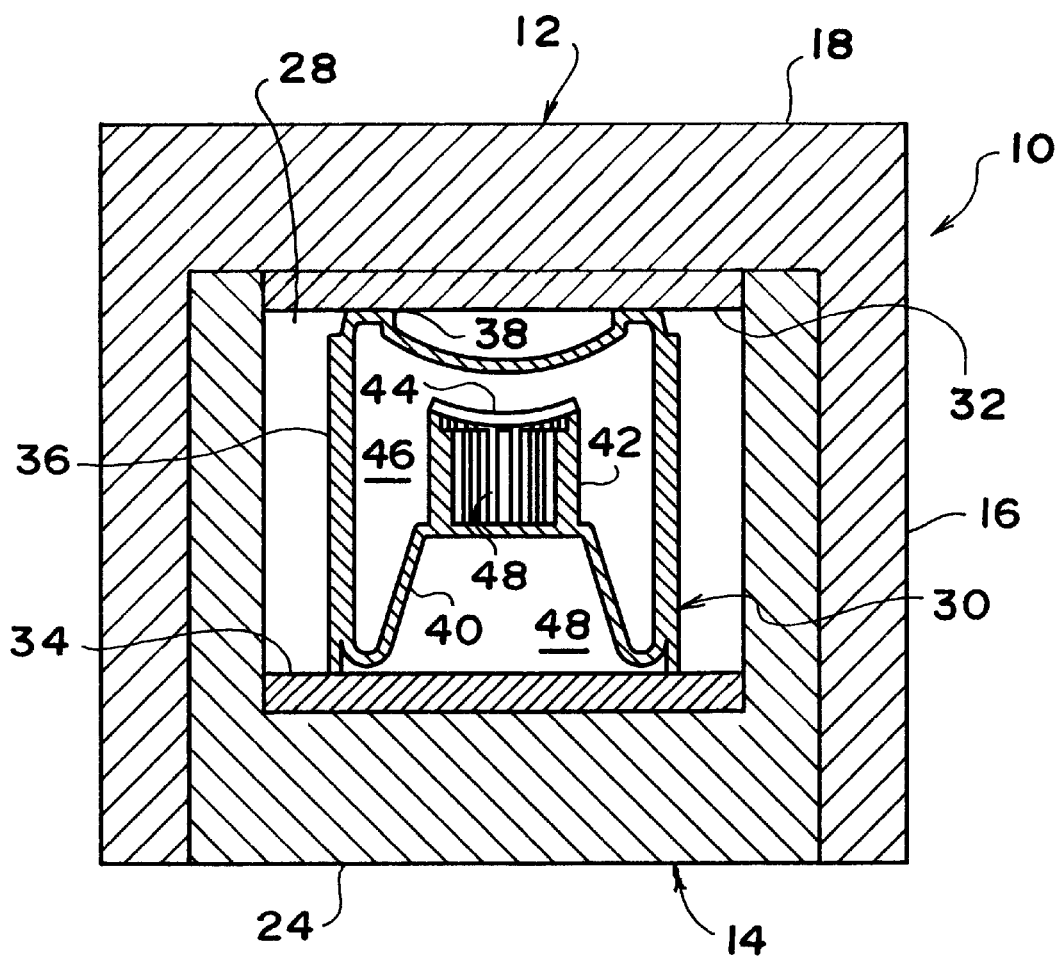
FIG. 1 is a schematic cut-away representation of a container of the present invention.
Figure 3:
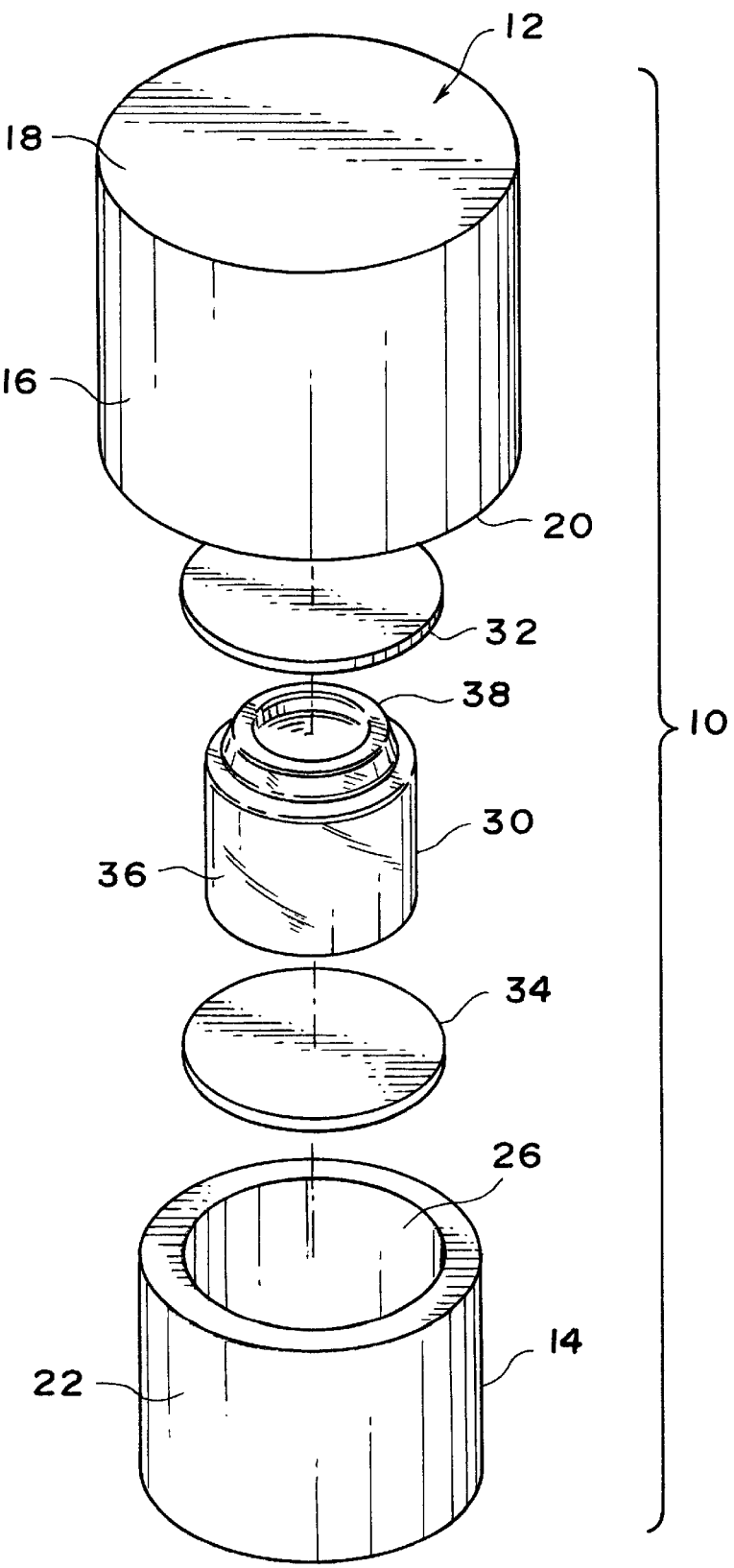
FIG. 3 is an exploded schematic representation of the container.

FIG. 1 and FIG. 3 show a container 10 for transporting temperature sensitive materials according to the invention. Container 10 includes outer insulating container body 12 and inner insulating container body 14. Outer insulating container body 12 is receptacle-shaped, comprising cylindrical wall 16, flat top cap 18 and open end 20 (shown in FIG. 3). Similarly, inner insulating container body 14 includes cylindrical wall 22, flat bottom base 24 and open end 26 (shown in FIG. 3). Body 14 is reduced in size compared to body 12 and is receptacle-shaped in a complementary manner to fit in interlocking nested engagement with body 12 to form hermetic chamber 28. In FIG. 1, the bodies 12 and 14 are shown nested with open ends 20, 26 (shown in FIG. 3) in opposing relationship to one another. The nesting receptacle-shaped bodies 12 and 14, can frictionally fit one body to the other or the bodies can be closed together by a rubber gasket, tape, shrink wrap or by a mechanical fastening device to form the hermetic chamber 28 (shown in FIG. 1).

Both body 12 and body 14 are constructed from materials that provide at least two functions. The materials are rigid materials that contribute structural integrity to the container 10 so that the container can be used for transporting materials. Additionally, the materials are insulating materials that have a low thermal conductivity to retard the passage of heat. The material conductivity should be less than about 0.1 (W/m K), however the material can be chosen to have a thermal conductivity of less than about 0.05 (W/m K) and even less than about 0.02 (W/m K).

Figure 2:
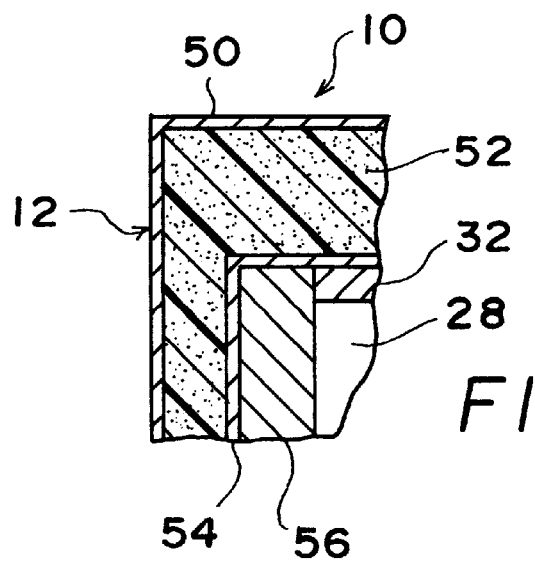
FIG. 2 is a section of one embodiment of the container.

Body 12 and body 14 can be solid or hollow. If hollow, the structure can be filled with a coolant or insulating material. FIG. 2 shows outer body shell 50 enclosing an insulating material 52 and inner shell 54 enclosing insulating material 56, which can be the same or a different insulation material than material 50.

In one embodiment, body 12 or body 14 is a PVC shell filled with an insulating material such as foamed or cellular polymeric material such as polystyrene, polyurethane and polyvinyl chloride. In another embodiment, the body 12 or body 14 is a cast structure from glass fiber, cellulosic material, mineral fiber, polymer gel or silicone rubber. Both body 12 and body 14 can be a solid insulating material or both can be a hollow structural material filled with a coolant or with an insulating material. In one embodiment, the outer body 12 comprises a hollow structural material filled with an insulating material and body 14 comprises a solid insulating material.

Hermetic chamber 28 forms a spacing to accommodate a specimen receiving structure such as a container 30. In the embodiment shown in FIG. 1 and FIG. 3, hermetic chamber 28 also encompasses compressible top disk 32 and compressible bottom disk 34, which can be constructed from insulating structural material and shock absorbing material to provide further resistance to thermal conductivity and to provide shock dampening to the specimen container 30. Suitable compressible materials for disks 32 and 34 include neoprene, sponge rubber and a compressible silicone, polystyrene or polyurethane.

Specimen container 30 includes cylindrical sidewall 36 and circular retaining lug 38. In a preferred embodiment as shown in FIG. 1 and FIG. 3, cylindrical sidewall 36 and circular retaining lug 38 provide a press fit between outer insulating container body 12 and inner insulating container body 14 (or disks 32, 34 as the case may be). The press fit provides a stable and secure positioning of specimen container 30 within hermetic chamber 28 (shown in FIG. 1).

The specimen container 30 also includes bottom pedestal 40, which supports specimen collector 42. Specimen collector 42 defines a specimen storage or viewing chamber. The collector 42 is an enclosure that is open only at its top end 44 to receive a specimen. The cavity size of the collector 42 can vary in shape and in size according to the object that is to be transported. In a preferred embodiment as shown in FIG. 1, the interior of the specimen collector 42 is smooth walled and free from encroaching projections so as to accommodate a corneal tissue specimen.

Hermetic chamber 28 can be filled with an insulating material having low thermal conductivity. Suitable materials include polymeric foams and fluids such as air or water at atmospheric or reduced pressure. The specimen container 30 and specimen collector 42 form interconnecting cavities 46 and 48 that can be filled with a protective and/or nutrient fluid to safeguard the transported corneal tissue. The protective nutrient fluid can be a tissue preservative media such as Optisol® corneal tissue storage media (Chiron Corporation, Emeryville, California) or a fluid with a low freezing point such as water and an alcohol such as ethylene glycol or ethanol and combinations thereof or tissue or a viral transport media such as saline. Exemplary fluids with low freezing points include glycols such as ethylene glycol and propylene glycol and alcohols such as ethanol, propanol and glycerol and mixtures of the glycols and/or alcohols and mixtures of the glycols and/or alcohols with water. In one embodiment the fluid in cavities 46 and 48 is the same fluid as in hermetic chamber 28. In another embodiment, a coolant or bag of coolant is placed in the hermetic chamber FIG. 4 and FIG. 5 show still another embodiment of the invention. Like structures in FIG. 4 and FIG. 5 are identified with like numerals to the structures of FIG. 1 and FIG. 3. In FIG. 4 and FIG. 5, container 10 includes outer insulating container body 12 and inner insulating container body 14. Outer insulating container body 12 is receptacle-shaped, comprising cylindrical wall 16, flat top cap 18 and open end 20. Similarly, inner insulating container body 14 includes cylindrical wall 22, flat bottom base 24 and open end 26. Body 14 and body 12 fit in interlocking nested engagement to form hermetic chamber 28. The container 10 encloses a different specimen collector 58, comprising a disk 60 perforated with apertures 62 to hold tube structures 64. The tube structures 64 hold transported specimens. The disk 60 is situated within the hermetic chamber 28 by press fit against the inner cylindrical wall 22 of inner insulating container body 14.

While preferred embodiments of the invention have been described, the present invention is capable of variation and modification and therefore should not be limited to the precise details of the examples. For example, disks 32, 34, can be modified in size and shape to accommodate a specimen container 30 for any fragile material for shipping. The invention includes changes and alterations that fall within the purview of the following claims.

What is claimed:

1. A container for transporting temperature sensitive materials, comprising:
   an outer insulating container body having a top and sidewall to form a receptacle shape;
   an inner insulating container body having a bottom and sidewall to form a receptacle shape to fit in interlocking nested engagement with said outer insulating container body to form a double walled hermetic chamber
   wherein said sidewalls extend to form a double wall along the entire hermetic chamber; and
   a specimen collector supported within said hermetic chamber.

2. The container of claim 1, wherein said specimen collector is a sealable liquid tight structure for receiving a corneal tissue specimen.

3. The container of claim 1, wherein said specimen collector is supported by a specimen container that is held in press fit between a pair of compressible disks within said hermetic chamber.

4. The container of claim 1, wherein said inner insulating container body is shaped for press fit nested engagement with said outer insulating container body to form said hermetic container.

5. The container of claim 1, wherein said inner insulating container body is held in nested engagement within said outer insulating container body by a rubber gasket, tape, shrink wrap, glue or cement to form said hermetic container.

6. The container of claim 1, wherein said inner insulating body is shaped complementary to said receptacle-shape of said outer insulating container body to fit in opposing relationship within said outer insulating container body in nested engagement.

7. The container of claim 1, wherein said outer insulating body and said inner insulating body are constructed from a rigid material having a thermal conductivity at least less than 0.1 (W/m K).

8. The container of claim 1, wherein said outer insulating body and said inner insulating body are constructed from a rigid material having a thermal conductivity at least less than 0.05 (W/m K).

9. The container of claim 1, wherein said outer insulating body and said inner insulating body are constructed from a rigid material having a thermal conductivity at least less than 0.02 (W/m K).

10. The container of claim 1, wherein at least one of said insulating bodies comprises cellular polymeric material or mineral fiber.

11. The container of claim 1, wherein at least one of said insulating bodies comprises polystyrene, polyurethane or polyvinyl chloride.

12. The container of claim 1, wherein at least one of said insulating bodies comprises a cast structure from glass fiber, cellulosic material, mineral fiber, polymer gel or silicone rubber.

13. The container of claim 1, wherein at least one of said insulating bodies comprises a hard shell filled with an insulating material.

14. The container of claim 1, wherein at least one of said insulating bodies comprises a hard shell filled with a coolant material.

15. The container of claim 3, wherein said specimen container defines a cavity and includes a pedestal to support said specimen collector.

16. The container of claim 1, wherein said specimen collector comprises a specimen chamber having an open top and sized and shaped to accommodate a corneal tissue.

17. The container of claim 1, wherein said specimen collector comprises a disk perforated with at least one aperture to hold a tube structure.

18. The container of claim 1, wherein said hermetic chamber is filled with a protective fluid to safeguard a transported corneal tissue.

19. The container of claim 1, wherein said hermetic chamber is filled with a protective fluid selected from the group consisting of alcohol, glycol and water to safeguard a transported corneal tissue.

20. The container of claim 1, wherein a coolant packing material is included within said hermetic chamber.

21. The container of claim 1, wherein said specimen collector is shaped to accommodate a corneal tissue.

22. A container for transporting temperature sensitive materials, comprising:

an outer insulating container body having a top and sidewall to form a receptacle shape;

an inner insulating container body having a bottom and sidewall to form a receptacle shape to fit in interlocking nested engagement with said outer insulating container body to form a double walled hermetic chamber; and a specimen container supported within said hermetic chamber and held in press fit between a pair of compressible disks within said hermetic chamber.

* * * * *